United States Patent
Kajiki et al.

(10) Patent No.: US 9,035,258 B2
(45) Date of Patent: May 19, 2015

(54) TOMOGRAPHY APPARATUS AND ELECTROMAGNETIC PULSE TRANSMITTING APPARATUS

(75) Inventors: Kousuke Kajiki, Tokyo (JP); Toshihiko Ouchi, Machida (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 114 days.

(21) Appl. No.: 13/977,802

(22) PCT Filed: Dec. 20, 2011

(86) PCT No.: PCT/JP2011/080145
§ 371 (c)(1),
(2), (4) Date: Jul. 1, 2013

(87) PCT Pub. No.: WO2012/093615
PCT Pub. Date: Jul. 12, 2012

(65) Prior Publication Data
US 2014/0264038 A1    Sep. 18, 2014

(30) Foreign Application Priority Data
Jan. 8, 2011 (JP) ................. 2011-002584

(51) Int. Cl.
*G01N 21/59* (2006.01)
*G01N 21/3581* (2014.01)
*G01N 21/55* (2014.01)
(Continued)

(52) U.S. Cl.
CPC ............ *G01N 21/59* (2013.01); *G01N 21/3581* (2013.01); *G01N 21/4795* (2013.01); *H01S 1/02* (2013.01); *G01N 21/55* (2013.01); *G01N 2021/1782* (2013.01); *G01N 2021/1787* (2013.01); *G01N 2021/558* (2013.01)

(58) Field of Classification Search
CPC .................. G01N 2021/1787; G01N 21/3581; G01N 2021/558; G01N 21/59
USPC ....................................... 250/341.3
See application file for complete search history.

(56) References Cited

U.S. PATENT DOCUMENTS 4,256,962 A * 3/1981 Horton et al. ................. 250/281
7,542,140 B2    6/2009 Ouchi et al. ................. 356/394
(Continued)

FOREIGN PATENT DOCUMENTS

EP    2 086 074 A2    8/2009
WO    WO 2005/088783 A1    9/2005

OTHER PUBLICATIONS

A.J. Fitzgerald et al., "Nondestructive Analysis of Tablet Coating Thicknesses Using Terahertz Pulsed Imaging," Journal of Pharmaceutical Sciences, vol. 94, No. 1, Jan. 2005, pp. 177-183.
(Continued)

*Primary Examiner* — David Porta
*Assistant Examiner* — Mindy Vu
(74) *Attorney, Agent, or Firm* — Fitzpatrick, Cella, Harper & Scinto (57) ABSTRACT

To provide an electromagnetic pulse transmitting apparatus and a tomography apparatus capable of shortening an electromagnetic pulse. The apparatus performs processing such that two electromagnetic pulse portions emitted to an object have an electric field intensity of mutually opposite polarity and the time difference between pulse peaks of the two electromagnetic pulse portions is a time difference within a time of a pulse width.

12 Claims, 6 Drawing Sheets

(51) Int. Cl.
  *G01N 21/47* (2006.01)
  *H01S 1/02* (2006.01)
  *G01N 21/17* (2006.01)

(56) References Cited

U.S. PATENT DOCUMENTS

| | | | | |
|---|---|---|---|---|
| 7,622,999 | B2 | 11/2009 | Koyama et al. | 331/107 T |
| 7,763,868 | B2 | 7/2010 | Ouchi et al. | 250/493.1 |
| 7,858,940 | B2 | 12/2010 | Ouchi | 250/341.1 |
| 7,907,024 | B2 | 3/2011 | Asada et al. | 331/107 T |
| 8,039,801 | B2 | 10/2011 | Kasai et al. | 250/341.1 |
| 2003/0012236 | A1* | 1/2003 | Hasson | 372/25 |
| 2003/0025917 | A1* | 2/2003 | Suhami | 356/601 |
| 2009/0178483 | A1* | 7/2009 | Angelsen et al. | 73/597 |
| 2009/0281736 | A1* | 11/2009 | Kim | 702/34 |
| 2013/0037721 | A1 | 2/2013 | Ouchi | 250/353 |

OTHER PUBLICATIONS

L. Ho et al., "Effects of film coating thickness and drug layer uniformity on in vitro drug release from sustained-released coated pellets: A case study using terahertz pulsed imaging," *International Journal of Pharmaceutics*, vol. 382, No. 1-2, Dec. 1, 2009, pp. 151-159.

Z. Li et al., "Ultrafast optical differentiators based on asymmetric Mach-Zehnder interferometer," *Proceeding Symposium IEEE/LEOS Benelux Chapter*, Eindhoven, 2006, pp. 173-176.

R. Yano et al., "Synthesis of terahertz electromagnetic wave pulses using amplitude-and-phase masks," *Chemical Physics*, vol. 326, Nos. 2-3, Aug. 1, 2006, pp. 577-582.

A. Sabatyan et al., "Retroreflector array as a tapped delay-line filter for ultra-short optical pulses," *Journal of the European Optical Society-Rapid Publications 1*, vol. 06022, Nov. 7, 2006, pp. 1-6.

R. Slavik et al., "Stable all-fiber photonic temporal differentiator using a long-period fibergrating interferometer," *Optics Communications*, vol. 282, No. 12, Jun. 15, 2009, pp. 2339-2342.

F. Zhang et al., "UWB Impulse Radio Transmitter Using an Electrooptic Phase Modulator Together With a Delay Interferometer," *IEEE Photonics Technology Letters*, vol. 22, No. 20, Oct. 15, 2010, pp. 1479-1481.

* cited by examiner

TOMOGRAPHY APPARATUS AND ELECTROMAGNETIC PULSE TRANSMITTING APPARATUS

TECHNICAL FIELD

The present invention relates to a tomography apparatus using an electromagnetic pulse, and more particularly to a tomography apparatus using a terahertz wave containing an electromagnetic component having a frequency domain of a millimeter-wave band to a terahertz band (30 GHz to 30 THz), and an electromagnetic pulse transmitting apparatus that transmits an electromagnetic pulse usable in such an apparatus.

BACKGROUND ART

In recent years, a non-destructive sensing technique using a terahertz wave has been developed. As an application field of the electromagnetic wave of this frequency band, there is an imaging technique for a safe tomography apparatus instead of an X-ray apparatus. Examples of the tomographic imaging method include a method in which an electromagnetic pulse is transmitted to a sample, and the reflected time waveform is measured to calculate the distance between two interfaces of the sample from the time difference of each electromagnetic pulse reflected on the two interfaces (Time-of-Flight method).

An example of the tomographic imaging method includes a technique disclosed in Non Patent Literature 1. The Non Patent Literature 1 discloses a technique for imaging a coating of a tablet using a terahertz pulse. According to the technique of the Non Patent Literature 1, a terahertz pulse emitted to a coated tablet is reflected on an interface between air and the coating and an inside interface between the coating and the tablet. As a result, the measured time waveform of a reflected terahertz wave includes two peaks corresponding to the two interfaces. Assuming that Δt denotes the time interval between the two peaks, the coating width d can be expressed by the following expression.

$$2d = \Delta t c / n$$

where c denotes the speed of light in a vacuum, and n denotes the refractive index of the coating material. The measured coating width is about several 10 μm. The Non Patent Literature 1 discloses an example of measuring the correlation between the coating width calculated by the aforementioned method and the drug release rate.

CITATION LIST

Non Patent Literature

NPL 1: Journal Of Pharmaceutical Sciences, VOL. 94, NO. 1, 2005. International Journal of Pharmaceutics, 382, 151-159, 2009.

SUMMARY OF INVENTION

Technical Problem

The narrower the pulse width of an electromagnetic pulse, the more the depth resolution of tomographic imaging by the Time-of-Flight method increases. According to the method disclosed in the Non Patent Literature 1, the terahertz pulse emitted from the light source is used for imaging as is without pulse shortening. Thus, the depth resolution needs more improvement.

Solution to Problem

In view of the above problem, the tomography apparatus of the present invention includes: a light source that generates an electromagnetic pulse; a detection section; an optical system that guides the electromagnetic pulse to the detection section; a processing section; and an electromagnetic pulse shaping section. The detection section detects the electromagnetic pulse. The processing section calculates a time waveform of the electromagnetic pulse from a signal transmitted from the detection section. The electromagnetic pulse shaping section is provided in an optical path reaching the detection section. The electromagnetic pulse shaping section divides the electromagnetic pulse into a plurality of electromagnetic pulse portions in such a manner that when transmitted, an electromagnetic pulse portion includes a portion having an electric field intensity of mutually opposite polarity and has a time difference within the time of a pulse width of the electromagnetic pulse.

In view of the above problem, further, the electromagnetic pulse transmitting apparatus of the present invention includes: a light source that generates an electromagnetic pulse; and an electromagnetic pulse shaping section. The electromagnetic pulse shaping section is provided in an optical path from the light source. The electromagnetic pulse shaping section divides the electromagnetic pulse into a plurality of electromagnetic pulse portions in such a manner that when transmitted, an electromagnetic pulse portion includes a portion having an electric field intensity of mutually opposite polarity and has a time difference within the time of a pulse width of the electromagnetic pulse.

Advantageous Effects of Invention

The present invention has the aforementioned electromagnetic pulse shaping section and hence can shorten the electromagnetic pulse emitted from the light source with a simple configuration. As a result, the present invention can provide tomographic imaging of improved depth resolution.

Further features of the present invention will become apparent from the following description of exemplary embodiments with reference to the attached drawings.

DESCRIPTION OF EMBODIMENTS

The present invention is characterized in that an electromagnetic pulse shaping section is used to divide an electromagnetic pulse in such a manner that a divided electromagnetic pulse portion includes a pulse portion having an electric field intensity of mutually opposite polarity and has a time difference within the time of a pulse width of the original electromagnetic pulse. The electromagnetic pulse shaping section may be any configuration as long as the electromagnetic pulse shaping section can divide the electromagnetic pulse into a plurality of electromagnetic pulse portions in such a manner that an electromagnetic pulse portion at the time of transmission includes a portion having an electric field intensity of mutually opposite polarity and has a time difference within the time of a pulse width of the electromagnetic pulse. The later described embodiments will focus on a simple configuration example having a plurality of interfaces contacting materials of different refractive index. However, the present invention is not limited to such a configuration, but, for example, may include a configuration in which an electromagnetic pulse is spatially divided into a plurality of electromagnetic pulse portions by a beam splitter or the like and each of the plurality of electromagnetic pulse portions is joined again through a different optical path. Such a configuration satisfies the polarity and time difference conditions in such a manner that at least one optical path of the different optical paths includes an optical delay system such as a movable and folded optical system capable of changing the optical path length, and the difference in the number of polarity reversal sections such as a total reflection mirror located in each optical path is odd. The number of electromagnetic pulse portions to be divided is typically two, but may be three or more. In order to divide the electromagnetic pulse into three or more portions, the polarity and the time difference of each electromagnetic pulse portion may be appropriately set as needed based on the principle in FIG. 2 described later. The frequency of the electromagnetic pulse includes not only a terahertz band but also a millimeter-wave band and a microwave band.

The electromagnetic pulse shaping section includes, for example, a first region; a second region contacting the first region; a third region; and a fourth region contacting the third region, as described later. Such a configuration is used to divide an original electromagnetic pulse into at least two portions: an electromagnetic pulse portion passing through the first region and reaching an interface with the second region; and an electromagnetic pulse portion passing through the third region and reaching an interface with the fourth region.

Now, referring to the accompanying drawings, embodiments and examples of the tomography apparatus and the electromagnetic pulse transmitting apparatus of the present invention will be described.

First Embodiment

Figure 1:
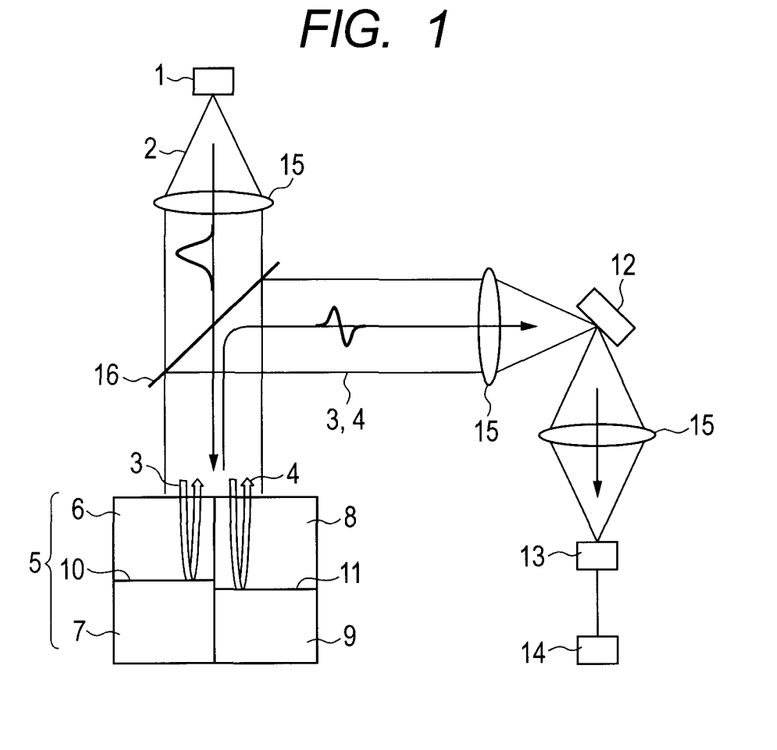
FIG. 1 is an overall outline drawing of a tomography apparatus according to a first embodiment of the present invention.

The tomography apparatus and the electromagnetic pulse transmitting apparatus according to a first embodiment of the present invention will be described referring to FIG. 1. In the configuration of FIG. 1, a light source 1 of the electromagnetic pulse transmitting apparatus generates an electromagnetic pulse 2. Examples of the light source 1 may include a light source that emits a femtosecond laser beam with a wavelength of 1.5 µm band when a voltage is applied to a photoconductive element. The electromagnetic pulse 2 is formed into a beam with an appropriate diameter by an optical system 15 and is incident into an electromagnetic pulse shaping section 5.

According to the present embodiment, the electromagnetic pulse shaping section 5 of the electromagnetic pulse transmitting apparatus includes a first region 6; a second region 7 contacting the first region 6; a third region 8; and a fourth region 9 contacting the third region 8. Inside the electromagnetic pulse shaping section 5, the electromagnetic pulse 2 is divided into an electromagnetic pulse 3 passing through the first region 6 and reaching an interface 10 between the first region 6 and the second region 7; and an electromagnetic pulse 4 passing through the third region 8 and reaching an interface 11 between the third region 8 and the fourth region 9. Each of the electromagnetic pulse 3 and the electromagnetic pulse 4 is an electromagnetic pulse portion that is reflected on the interface 10 and the interface 11 respectively and is transmitted from the electromagnetic pulse shaping section 5. Then, the electromagnetic pulse 3 and the electromagnetic pulse 4 are emitted to a sample 12 by an optical system 15. In FIG. 1, the electromagnetic pulses 3 and 4 are shaped by the electromagnetic pulse shaping section 5, pass through an optical system, and reach the optical system 15. Then, the electromagnetic pulse 3 and the electromagnetic pulse 4 reflected on the sample 12 are made incident into detection section 13 by the optical system 15. Specifically, there is provided an optical system that irradiates the sample 12 with a plurality of electromagnetic pulse portions transmitted from the electromagnetic pulse shaping section 5 and guides the electromagnetic pulse portions reflected on or transmitted through the sample to a detection section 13. The detection section 13 detects the electric field intensity of the incident electromagnetic wave. Examples of the detection section 13 may include a detection section that irradiates the photoconductive element with a femtosecond laser beam with a wavelength of 1.5 µm band and measures a current flowing between the electrodes of the photoconductive element.

The two electromagnetic pulses 3 and 4 are processed by the electromagnetic pulse shaping section 5 so that the polarity of the electric field intensity is mutually opposite and the time difference between the pulse peaks is within the time of the pulse width of the electromagnetic pulse 2 in the detection section 13. A specific configuration of the electromagnetic pulse shaping section 5 having such a function will be described later. In this description, the time of a pulse width refers to the FWHM (Full Width at Half Maximum) of the electric field intensity of the electromagnetic pulse 2. In the detection section 13, the electromagnetic pulse 3 and the electromagnetic pulse 4 are incident on the same detection element. As a result, the detection section 13 detects a combined electric field intensity of the electromagnetic pulse 3 and the electromagnetic pulse 4. The detected electric field intensity is sent to a processing section 14 which calculates a time waveform thereof. A so-called time-domain spectroscopy can be used to detect the time waveform of such an electric field intensity. The processing section 14 can build, for example, an image in the depth direction of the sample 12 from the time waveform. Note that while in this embodiment the electromagnetic pulse 3 and the electromagnetic pulse 4 are spatially overlapped and incident on the same detection element in the detection section 13, only a part thereof may be spatially overlapped in the detection section 13 or the electromagnetic pulse 3 and the electromagnetic pulse 4 may be close but not overlapped in the detection section 13. Even in a partially overlapped or non-overlapped state in the detection section 13, as long as the irradiation position of the electromagnetic pulses 3 and 4 can be considered as a position of substantially the same state in the sample 12, the combined electric field intensity of the pulses 3 and 4 can be detected in the position of the same state. Specifically, even in such a state, the detection section 13 can obtain information about the sample portion considered as the position of the same state with an effect of improved depth resolution by electrically overlapping and processing a signal by the electromagnetic pulses 3 and 4. Therefore, at least a part of the electromagnetic pulses 3 and 4 may be spatially overlapped or none thereof may be overlapped in a position of substantially the same state in the sample. Note that in a case in which the electromagnetic pulses 3 and 4 are emitted to positions of different states of the sample, electrically overlapping and processing a signal by these pulses in the detection section is useless because no information about these positions is provided. Thus, preferably at least a part of the plurality of electromagnetic pulse portions is spatially overlapped in the detection section or at least a part thereof is spatially overlapped in the sample.

Figure 2:
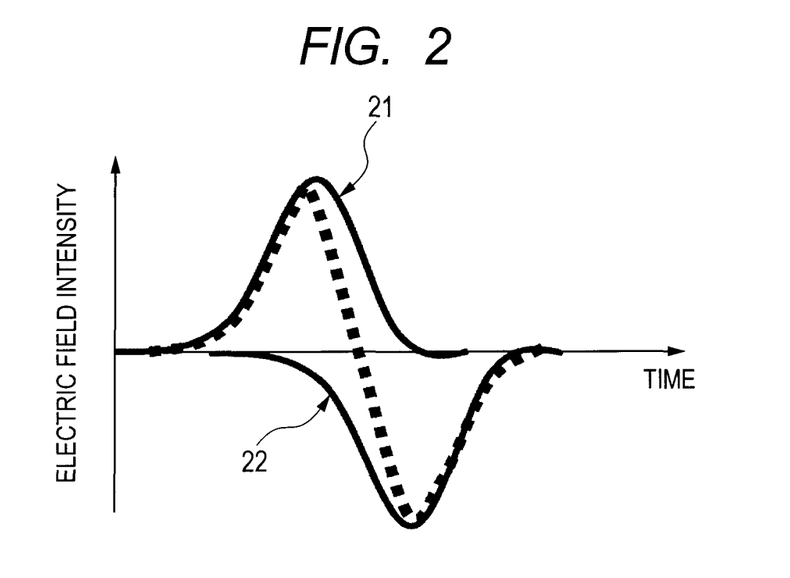
FIG. 2 is a principle drawing for pulse shortening of an electromagnetic pulse according to the present invention.

Next, the principle of pulse shortening will be described. FIG. 2 illustrates a principle drawing of pulse shortening. The horizontal axis indicates time and the vertical axis indicates electric field intensity. As illustrated by the solid lines, a time waveform 21 of one electromagnetic pulse portion and a time waveform 22 of the other electromagnetic pulse portion have a different polarity of the electric field intensity (namely, an opposite direction of the electric field) and the time difference between the pulse peaks is within the time of the original pulse width. The dotted line in FIG. 2 indicates a combined time waveform of the time waveform 21 of one electromagnetic pulse portion and the time waveform 22 of the other electromagnetic pulse portion. It is understood that the pulse is shortened because the right side portion of the peak of the time waveform 21 of one electromagnetic pulse portion is cancelled by the time waveform 22 of the other electromagnetic pulse portion. Here, if the two pulse portions are far away from the time of the original pulse width, the time domain for cancelling the two pulse portions is reduced, leading to a reduction in pulse shortening effect. Thus, the present invention provides pulse shortening by reversing the polarity of the electric field intensity of the electromagnetic pulse 3 and the electromagnetic pulse 4 and providing the electromagnetic pulse 3 and the electromagnetic pulse 4 with a time difference within the time of the original pulse width.

The polarity of the electric field intensity of the electromagnetic pulse 3 and the electromagnetic pulse 4 is reversed using a principle that when an electromagnetic wave is reflected on an interface between the two materials, the polarity of the electric field intensity of the reflected electromagnetic wave depends on the relationship in magnitude between the refractive indexes of the two materials in the wavelength range of the electromagnetic wave. According to the Fresnel equations given in the following expression 1, when a refractive index nA of an incident-side material of the electromagnetic wave is less than a refractive index nB of another material forming an interface therebetween, the polarity of the electric field intensity of the reflected electromagnetic wave is reversed from the polarity of the incident electromagnetic wave. Meanwhile, when the refractive index nA is greater than the refractive index nB, the polarity of the electric field intensity of the reflected electromagnetic wave is the same as the polarity of the incident electromagnetic wave.

$$r = (nA - nB)/(nA + nB) \qquad \text{Expression 1}$$

where r denotes the field reflectance, nA denotes the refractive index of the incident-side material, and nB denotes the refractive index of another material forming the interface therebetween.

Examples of the material for the refractive index nB forming the interface may include metal. For example, gold can be used assuming that its refractive index is approximately infinite with respect to the electromagnetic wave of the terahertz band. The electromagnetic pulse has a wide spectrum, and the major shape of the time waveform depends on a component of a large electric field intensity on the spectrum. Therefore, the relationship between the refractive indexes of the two materials may be satisfied by the component of a large electric field intensity on the spectrum. For example, the relationship may be satisfied in a frequency domain from a maximum electric field intensity to minus 3 dB or more on the spectrum. Apparently, the relationship between the refractive indexes is preferably desired to be satisfied in a wider range of the spectrum of the electromagnetic pulse.

Next, in order to cause the electromagnetic pulse 3 and the electromagnetic pulse 4 to have a time difference, an optical path length difference may be given between the two pulses. The optical path length OL is given as OL=n×L, where n denotes the refractive index of a material through which the electromagnetic wave propagates, and L denotes the propagation distance. Thus, in order to change the optical path length, the refractive index of the propagating material may be changed or the propagation distance may be changed. In order to cause the time difference between the pulse peaks to be within the time of the pulse width of the electromagnetic pulse 2, for example, assuming that the pulse width of the electromagnetic pulse 2 is 300 fs, the optical path length difference may be set between the two pulse portions only by the optical path length 90 μm or less corresponding to the original pulse width.

Figure 3:
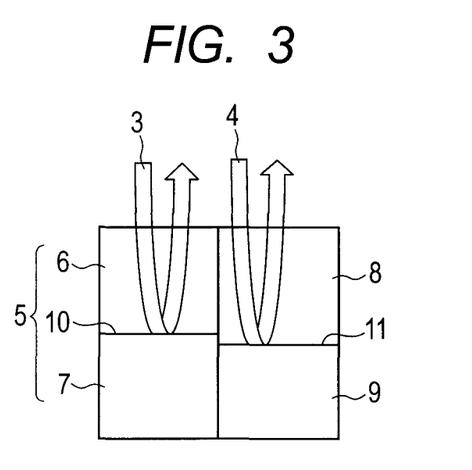
FIG. 3 is a drawing illustrating a configuration example of an electromagnetic pulse shaping section according to the first embodiment.
Figure 4:
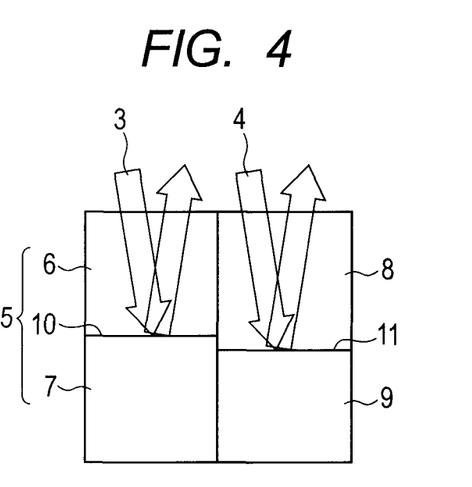
FIG. 4 is a drawing illustrating another configuration example of an electromagnetic pulse shaping section according to the first embodiment.

FIG. 3 illustrates an example of the configuration of the electromagnetic pulse shaping section 5. In such a configuration in which the electromagnetic pulse 3 and the electromagnetic pulse 4 are reflected to the incident side of the electromagnetic pulse 2, in order to mutually reverse the polarity of the electromagnetic pulse 3 and the electromagnetic pulse 4, the refractive indexes need to satisfy the relation: n1<n2 and n3>n4; or n1>n2 and n3<n4, where n1 denotes the refractive index of the first region 6, n2 denotes the refractive index of the second region 7, n3 denotes the refractive index of the third region 8, and n4 denotes the refractive index of the fourth region 9. FIG. 3 illustrates an example in which the electromagnetic pulse is incident perpendicular to the interface 10 and the interface 11 of the electromagnetic pulse shaping section 5, but the electromagnetic pulse may be incident obliquely to the interfaces as illustrated in FIG. 4. This configuration can prevent the optical axis of the electromagnetic pulse incident into the electromagnetic pulse shaping section 5 from being overlapped with the optical axis of the electromagnetic pulse transmitted from the electromagnetic pulse shaping section 5. Thus, the configuration eliminates the need of a beam splitter for separating the optical axis of the two pulses and has an advantage of reducing power loss. Note that in this case, consideration needs to be made about the propagation distance L which is obtained by dividing the distance between the interfaces by cos α, where α denotes the incident angle of the electromagnetic pulse incident on the interface.

As described above, the tomography apparatus of the present embodiment can use shortened electromagnetic pulses to perform tomography and obtain tomographic images. The pulse shortening can generally improve the depth resolution of tomography using the Time-of-Flight method and hence the tomography apparatus of the present embodiment can obtain tomographic images of improved depth resolution.

A further specific example of the first embodiment will be described.

First Example

As a design example of the tomography apparatus and the electromagnetic pulse transmitting apparatus of the first example, the detail of the electromagnetic pulse shaping section 5 and the acquired time waveform will be described. The outline of the tomography apparatus of the present example is the same as that illustrated in FIG. 1 (except that the sample 12 is not present for ease of illustrating pulse shortening effect). The light source 1 emitted a femtosecond laser beam with a wavelength of 1.5 μm band when a voltage was applied between the electrodes of LT (Low-Temperature)-InGaAs photoconductive elements. The detection section 13 converted the femtosecond laser beam with a wavelength of 1.5 μm band to a double wave through a nonlinear crystal to be emitted to the LT-GaAs photoconductive element. The time waveform of the terahertz pulse 2 was processed in the processing section 14 by measuring the current flowing between the electrodes of the photoconductive element of the detection section 13 while changing the relative delay time between the femtosecond laser beams on the generation side and the detection side according to a well-known terahertz time-domain spectroscopy.

Figure 5:
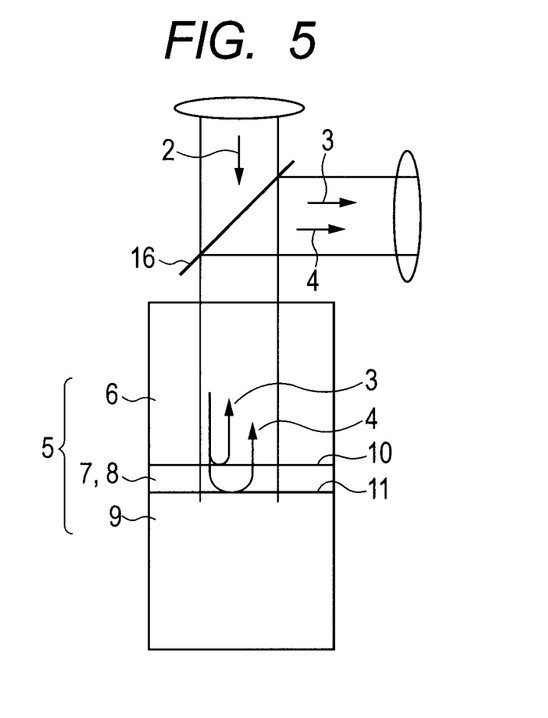
FIG. 5 is a drawing illustrating a configuration example of an electromagnetic pulse shaping section according to the first example of the present invention.

FIG. 5 illustrates a configuration of the electromagnetic pulse shaping section 5 used in the present example. In the present example, the second region 7 is integrated with the third region 8. Specifically, each region is serially arranged along the optical axis of the electromagnetic pulse. In contrast to this, in the electromagnetic pulse shaping section 5 illustrated in FIG. 1, the two regions are arranged parallel to each other along the optical axis of the electromagnetic pulse. Thereby, in the configuration of FIG. 5, a part of the electromagnetic pulse 2 is reflected on the interface 10 into the electromagnetic pulse 3, and another part thereof is reflected on the interface 11 into the electromagnetic pulse 4. The electromagnetic pulse 3 and the electromagnetic pulse 4 are transmitted from the electromagnetic pulse shaping section 5, and then the advancing direction thereof is changed by a beam splitter 16. Here, in order to reverse the polarity of the electromagnetic pulse 3 and the electromagnetic pulse 4, the refractive indexes need to satisfy the relation: $n1<n2$ and $n2>n4$; or $n1>n2$ and $n2<n4$, where n1 denotes the refractive index of the first region 6, n2 denotes the refractive index of the second region 7 (integrated with the third region 8 according to the present example), and n4 denotes the refractive index of the fourth region 9.

Figure 6:
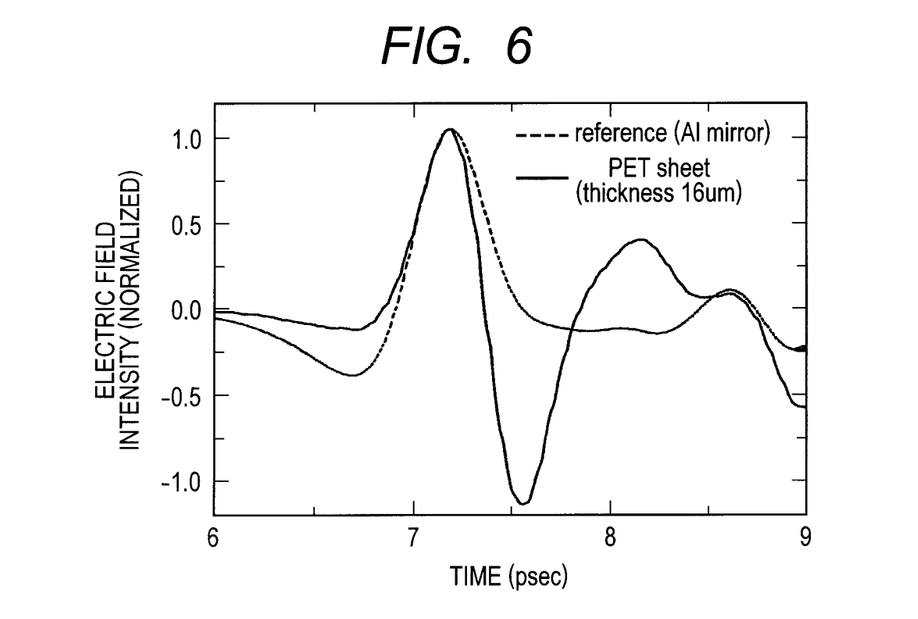
FIG. 6 is a drawing illustrating an example of a time waveform of an electromagnetic pulse obtained by the tomography apparatus of the present invention.

FIG. 6 illustrates an example of the time waveform of the electric field intensity of an electromagnetic pulse measured using the above configured tomography apparatus (excluding the sample 12 as described above). The FWHM (electric field intensity) of the electromagnetic pulse 2 emitted to the electromagnetic pulse shaping section 5 was 350 fs, and the major frequency range contained in the electromagnetic pulse 2 was about 0.1 to 5 THz. Further, the depth resolution obtained by tomographic measurement of the electromagnetic pulse 2 without passing through the electromagnetic pulse shaping section 5 was about 20 μm. The solid line indicates the time waveform of the reflected electromagnetic pulse when a polyethylene terephthalate (PET) sheet (with a thickness of 16 μm and a refractive index of 1.9) as the electromagnetic pulse shaping section 5 described in the present example was used. There was air (a refractive index of 1) outside the PET sheet. The PET sheet corresponds to the second region 7 and the third region 8. The air on the front side of the PET sheet (on the incident side of the electromagnetic pulse) corresponds to the first region 6, and the air on the back side of the PET sheet corresponds to the fourth region 9. The electromagnetic pulse 3 was reflected on the front surface of the PET sheet, and the electric field intensity of its peak was about 30 percent of the original electromagnetic pulse 2. Meanwhile, the electromagnetic pulse 4 was reflected on the back surface of the PET sheet, and the electric field intensity of its peak was about 30 percent of the original electromagnetic pulse 2. The electromagnetic pulses 3 and 4 had a mutually opposite polarity of the electric field intensity. The dotted line indicates the time waveform when the PET sheet was replaced with an aluminum mirror in the position of the electromagnetic pulse shaping section 5. The time waveform thereof corresponds to the time waveform of the electromagnetic pulse 2 when the electromagnetic pulse shaping section 5 was not used. According to FIG. 6, the FWHM of the electromagnetic pulse 2 (indicated by the dotted line) when the electromagnetic pulse shaping section 5 was not used was 350 fs, while the FWHM of the electromagnetic pulse 2 (indicated by the solid line) when the electromagnetic pulse shaping section 5 was used was 290 fs, which means that pulse shortening was achieved. This indicates that the FWHM of the electromagnetic pulse was reduced by 17% by the electromagnetic pulse shaping section 5. The pulse shortening of the electromagnetic pulse 2 improves the depth resolution for tomographic measurement. Assuming that for the sake of simplicity, the depth resolution is proportional to the pulse width, the depth resolution is expected to improve from 20 μm to 17 μm.

Second Embodiment

The second embodiment of the present invention relates to a tomography apparatus and an electromagnetic pulse transmitting apparatus using a transmission type electromagnetic pulse shaping section. The present embodiment will be described referring to FIG. 7. The present embodiment is characterized by being different from the first embodiment in that the advancing direction of the electromagnetic pulse 3 and the electromagnetic pulse 4 transmitted from the electromagnetic pulse shaping section 5 matches the advancing direction of the original electromagnetic pulse 2 incident into the electromagnetic pulse shaping section 5. The present embodiment has the same components as those of the first embodiment except the electromagnetic pulse shaping section 5. In order to achieve this characteristic, the present embodiment is configured such that the electromagnetic pulse 3 is not reflected on the interface 10 or the interface 11, while the electromagnetic pulse 4 is first reflected on the interface 11 and then is reflected on the interface 10.

Figure 7:
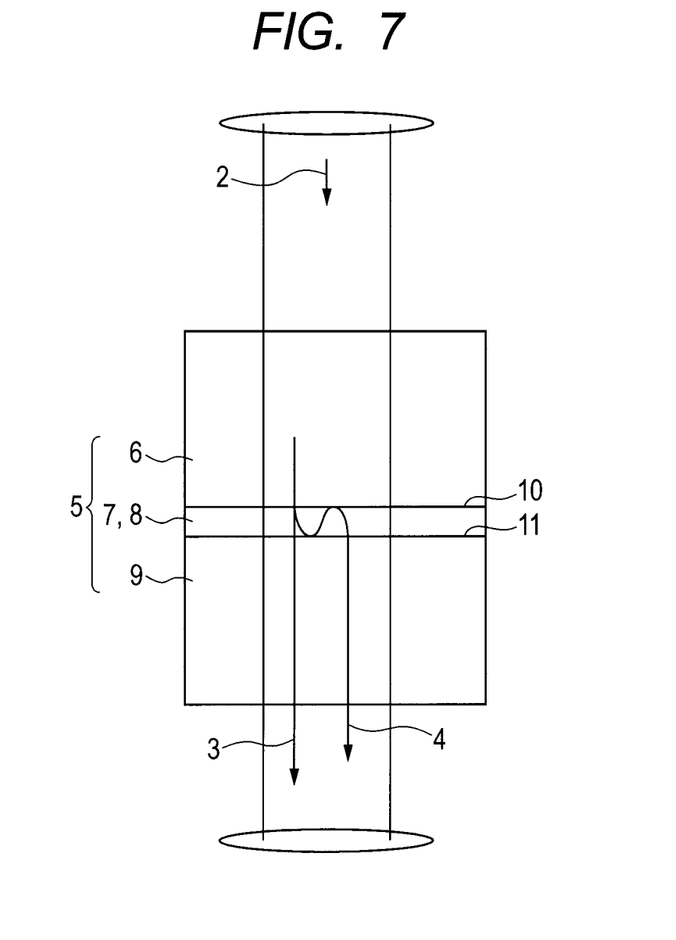
FIG. 7 is a drawing illustrating a configuration example of an electromagnetic pulse shaping section according to a second embodiment.

Here, in order to reverse the polarity of the electromagnetic pulse 3 and the electromagnetic pulse 4, the refractive indexes need to satisfy the relation: $n1<n2$ and $n2<n4$; or $n1>n2$ and $n2>n4$, where n1 denotes the refractive index of the first region 6, n2 denotes the refractive index of the second region 7 (integrated with the third region 8), and n4 denotes the refractive index of the fourth region 9. Examples of the material having the relation of the refractive indexes in the terahertz band include air ($n1=1$) for the first region 6, cycloolefin resin ($n2=1.5$) for the second region 7 (integrated with the third region 8), and silicon ($n4=3.4$) for the fourth region 9.

The present embodiment has been described using the configuration illustrated in FIG. 7, but for example, the electromagnetic pulse 2 may be obliquely incident on the interface 10 and the interface 11.

As described above, the tomography apparatus of the present embodiment can match the optical axis of the original electromagnetic pulse 2 with the divided optical axes of the electromagnetic pulse 3 and the electromagnetic pulse 4, thus simplifying the alignment of the optical system. Further, the present embodiment can avoid power loss because no beam splitter is used.

Third Embodiment

The third embodiment of the present invention relates to a tomography apparatus and an electromagnetic pulse transmitting apparatus using a variable time difference between the electromagnetic pulse 3 and the electromagnetic pulse 4. The present embodiment is characterized by being different from the first embodiment in that the optical path length difference between the electromagnetic pulse 3 and the electromagnetic pulse 4 is made variable in the electromagnetic pulse shaping section 5. The present embodiment has the same components as those of the first embodiment except the electromagnetic pulse shaping section 5.

The optical path length difference between the electromagnetic pulse 3 and the electromagnetic pulse 4 can be made variable by changing any one of the refractive indexes of the first region 6, the second region 7, the third region 8, and the fourth region 9 through which the electromagnetic wave propagates, or changing the propagation distance. The refractive index may be changed by changing the material in the optical path to another material having a different refractive index, using an electro-optical effect, or the like. The electro-optical effect may be used, for example, by controlling the voltage to be applied to any region made of an electro-optical material. The propagation distance may be changed by moving the relative position between the interface 10 and the interface 11 in a direction of the optical axis. Specifically, a movable unit using a mechanical method and a piezo method or so may be used to move the material forming one of the interfaces in a direction of the optical axis. Thus, the present embodiment includes a unit for adjusting the time difference between a plurality of electromagnetic pulse portions incident into the detection section.

Several electromagnetic pulse shaping sections 5 which can be exchangeable and have different optical path length differences may be included. A reduction in optical path length difference shortens the pulse but reduces the electric field intensity. The reduction in electric field intensity is due to the effect that the electromagnetic pulse 3 and the electromagnetic pulse 4 cancel the mutual electric field intensity. The smaller the pulse interval between the two pulses is, the more remarkable the effect is. This mode may be used to acquire an image of high depth resolution. Meanwhile, an increase in optical path length difference increases the electric field intensity but increases the pulse width (close to the pulse width of the original electromagnetic pulse 2). This mode may be used to acquire an image of high SN ratio.

As described above, the tomography apparatus of the present embodiment can use the electromagnetic pulse shaping section to select an imaging mode focusing on one of the depth resolution and the SN ratio. Thus, an imaging mode can be selected according to the object to be measured and hence high quality imaging can be performed.

Fourth Embodiment

The fourth embodiment of the present invention relates to a tomography apparatus and an electromagnetic pulse transmitting apparatus using the electromagnetic pulse 3 and the electromagnetic pulse 4 of different frequency spectral shapes. The present embodiment is characterized by being different from the first embodiment in that the electromagnetic pulse 3 and the electromagnetic pulse 4 as the divided electromagnetic pulse portions have different frequency spectral shapes.

Figure 8A:
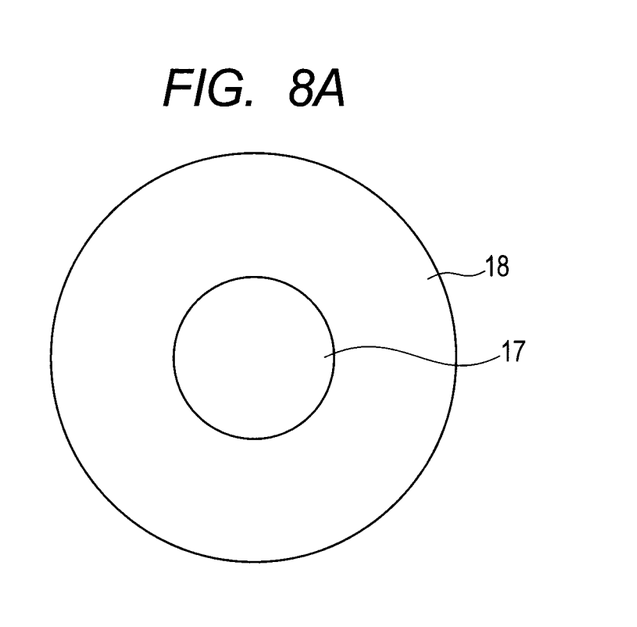
FIGS. 8A and 8B are drawings illustrating a configuration example of an electromagnetic pulse shaping section according to a fourth embodiment.
Figure 8B:
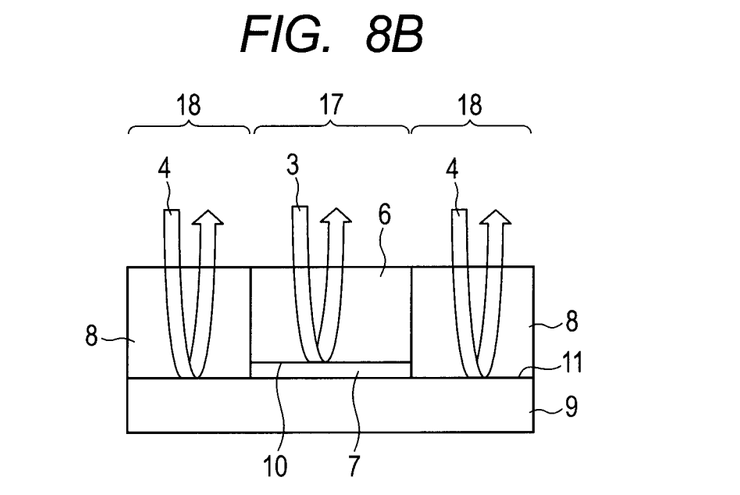

This characteristic may be achieved, for example, using the effect that when an electromagnetic pulse is focused, a low-frequency component is focused in a wider range than a high-frequency component. FIG. 8A illustrates the electromagnetic pulse shaping section 5 viewed along a direction of the optical axis of the electromagnetic pulse 2. FIG. 8B illustrates the electromagnetic pulse shaping section 5 viewed from a direction perpendicular to the optical axis thereof. An inside region 17 includes a first region 6 and a second region 7 contacting the first region 6 through an interface 10. An outside region 18 includes a third region 8 and a fourth region 9 contacting the third region 8 through an interface 11. The electromagnetic pulse 4 reflected on the interface 11 of the outside region 18 contains relatively more low-frequency components than the electromagnetic pulse 3 reflected on the interface 10 of the inside region 17. As described in the first embodiment, the two pulse portions are incident into the detection section 13 after the electric field intensity is mutually reversed and a time difference within the time of pulse width is given by the electromagnetic pulse shaping section 5.

Figure 9:
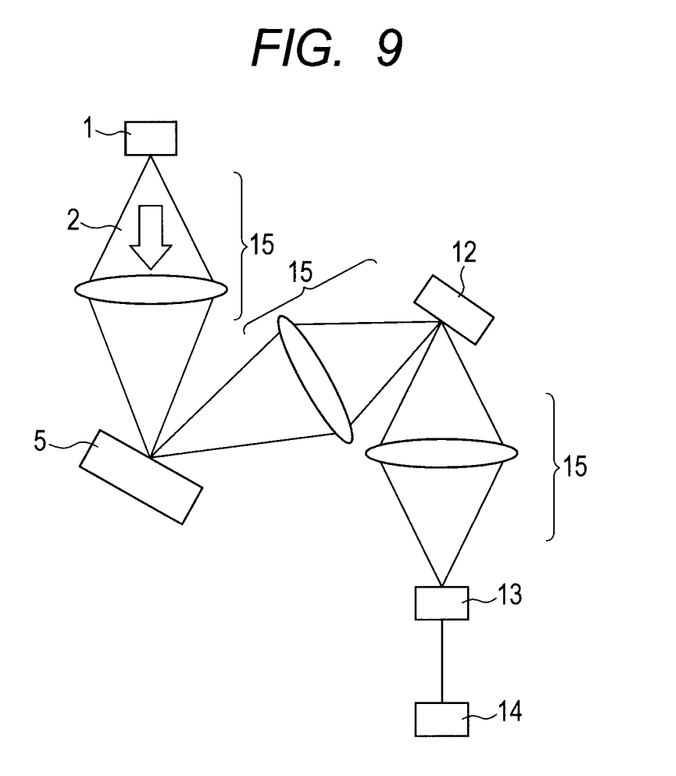
FIG. 9 is an overall outline drawing of a tomography apparatus according to the fourth embodiment of the present invention.

FIG. 9 is an overall outline drawing of the tomography apparatus including the electromagnetic pulse shaping section 5. The present embodiment is the same as the first embodiment except that the electromagnetic pulse 2 is focused and is incident into the electromagnetic pulse shaping section 5. FIG. 9 illustrates an example of using the focused electromagnetic pulse 2, but even collimated beams can achieve the characteristics of the present embodiment as long as the electromagnetic pulse 2 has a frequency distribution in the wavefront.

As described above, the tomography apparatus of the present embodiment can use the electromagnetic pulse 3 containing more high-frequency components and the electromagnetic pulse 4 containing more low-frequency components. Therefore, for example, high-frequency components contained in the original electromagnetic pulse 2 can be moved to the electromagnetic pulse 3 so as to have more high-frequency components for pulse shortening.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-002584, filed Jan. 8, 2011, which are hereby incorporated by reference herein in their entirety.

REFERENCE SIGNS LIST 1 light source
2 electromagnetic pulse
3, 4 electromagnetic pulse portion
5 electromagnetic pulse shaping section
6 first region
7 second region
8 third region
9 fourth region
10, 11 interface
13 detection section
14 processing section
15 optical system

The invention claimed is:

1. A tomography apparatus comprising:
   a light source that generates an electromagnetic pulse;
   a detection section that detects the electromagnetic pulse;
   an optical system that guides the electromagnetic pulse to the detection section;
   a processing section that calculates a time waveform of the electromagnetic pulse from a signal transmitted from the detection section; and
   an electromagnetic pulse shaping section which is provided in an optical path of the electromagnetic pulse from the light source to the detection section, and which divides the electromagnetic pulse into a plurality of electromagnetic pulse portions in such a manner that when transmitted from the electromagnetic pulse shaping section, the electromagnetic pulse portions have electric field intensities of mutually opposite polarities and have a time difference within a time of a pulse width which is a full width at half maximum of the electric field intensities of the electromagnetic pulse.

2. The tomography apparatus according to claim 1, wherein the electromagnetic pulse shaping section includes a first region, a second region contacting the first region, a third region, and a fourth region contacting the third region, and divides the electromagnetic pulse into at least two portions: an electromagnetic pulse portion passing through the first region and reaching an interface with the second region, and an electromagnetic pulse portion passing through the third region and reaching an interface with the fourth region.

3. The tomography apparatus according to claim 2, wherein the electromagnetic pulse shaping section satisfies:
   n1<n2 and n3>n4; or n1>n2 and n3<n4,
   where n1 denotes the refractive index of the first region, n2 denotes the refractive index of the second region, n3 denotes the refractive index of the third region, and n4 denotes the refractive index of the fourth region.

4. The tomography apparatus according to claim 2, wherein the electromagnetic pulse shaping section satisfies:
   n1<n2 and n3<n4; or n1>n2 and n3>n4,
   where n1 denotes the refractive index of the first region, n2 denotes the refractive index of the second region, n3 denotes the refractive index of the third region, and n4 denotes the refractive index of the fourth region.

5. The tomography apparatus according to claim 4, wherein an advancing direction of the electromagnetic pulse incident into the electromagnetic pulse shaping section matches the advancing direction of the electromagnetic pulse portion transmitted from the electromagnetic pulse shaping section.

6. The tomography apparatus according to claim 1, wherein at least a part of a plurality of the electromagnetic pulse portions is spatially overlapped in the detection section.

7. The tomography apparatus according to claim 1, further comprising an optical system that irradiates a sample with the electromagnetic pulse portions transmitted from the electromagnetic pulse shaping section, and guides, to the detection section, the electromagnetic pulse portions reflected on or transmitted through the sample.

8. The tomography apparatus according to claim 7, wherein at least a part of a plurality of the electromagnetic pulse portions is spatially overlapped in the sample.

9. The tomography apparatus according to claim 1, further comprising a unit for adjusting a time difference between a plurality of the electromagnetic pulse portions incident into the detection section.

10. The tomography apparatus according to claim 1, wherein the plurality of the electromagnetic pulse portions have different frequency spectral shapes.

11. An electromagnetic pulse transmitting apparatus comprising:
    a light source that generates an electromagnetic pulse; and
    an electromagnetic pulse shaping section which is provided in an optical path of the electromagnetic pulse from the light source, and which divides the electromagnetic pulse into a plurality of electromagnetic pulse portions in such a manner that when transmitted from the electromagnetic pulse shaping section, the electromagnetic pulse portions have an electromagnetic pulse portion having an electric field intensity of mutually opposite polarity and have a time difference within a time of a pulse width of the electromagnetic pulse.

12. The electromagnetic pulse transmitting apparatus according to claim 11, wherein the electromagnetic pulse shaping section includes a first region, a second region contacting the first region, a third region, and a fourth region contacting the third region; and divides the electromagnetic pulse into at least two portions: an electromagnetic pulse portion passing through the first region and reaching an interface with the second region, and an electromagnetic pulse portion passing through the third region and reaching an interface with the fourth region.

* * * * *